US00PP35652P2

(12) United States Plant Patent
Petter et al.

(10) Patent No.: US PP35,652 P2
(45) Date of Patent: Feb. 13, 2024

(54) GARLIC PLANT NAMED 'BGS 352'

(50) Latin Name: *Allium sativum*
Varietal Denomination: BGS 352

(71) Applicants: Bejo Zaden BV, Warmenhuizen (NL); De Groot en Slot BV, Broek op Langedijk (NL)

(72) Inventors: Timo Christiaan Petter, Warmenhuizen (NL); Lennaert Crispijn Aardse, Broek op Langedijk (NL)

(73) Assignees: De Groot en Slot BV, Warmenhuizen (NL); Bejo Zaden BV, Langedijk (NL)

( * ) Notice: Subject to any disclaimer, the term of this patent is extended or adjusted under 35 U.S.C. 154(b) by 39 days.

(21) Appl. No.: 18/126,559

(22) Filed: Mar. 27, 2023

(51) Int. Cl.
*A01H 5/00* (2018.01)
*A01H 6/56* (2018.01)

(52) U.S. Cl.
USPC ..... Plt./258

(58) Field of Classification Search
USPC ..... Plt./258
See application file for complete search history.

*Primary Examiner* — Karen M Redden
(74) *Attorney, Agent, or Firm* — The Webb law Firm

(57) ABSTRACT

A new and distinct variety of garlic plant with good eating and keeping qualities.

3 Drawing Sheets

Botanical classification: *Allium sativum.*
Varietal denomination: 'BGS 352'.

BACKGROUND OF THE INVENTION

The present invention comprises a new and distinct *Allium sativum* garlic plant known by the varietal name 'BGS 352'. The new variety is the result of a planned breeding program conducted in the Netherlands and was discovered in October of 2018. The purpose of the breeding program was to provide new and distinct garlic varieties for commercial use. 'BGS 352' is the result of the crossing of an *Allium sativum* variety referred to by the applicant as 0019 (female parent, unpatented) with an *Allium sativum* variety referred to by the applicant as 5000 (male parent, unpatented). The first act of asexual reproduction of 'BGS 352' was conducted in October of 2018 by splitting and replanting its cloves in soil in Broek op Langedijk, the Netherlands. 'BGS 352' has been trial and field tested and has been found to retain its distinctive characteristics and remain true to type through successive propagations. The present invention has not been evaluated under all possible environmental conditions. The phenotype may vary with variations in environment without a change in the genotype of the plant.

When compared to garlic variety named 'Germidour' (unpatented), 'BGS 352' is similar to 'Germidour' in bulb shape, ground color of dry external scales, and having anthocyanin stripes on dry external scales. However, 'BGS 352' has a pseudostem and 'Germidour' does not. Further, the scale color of 'BGS 352' is pink and the scale color of 'Germidour is brown.

When compared to other garlic varieties known to the applicant, 'BGS 352' can be distinguished based on its pink scale color and having a pseudostem.

DESCRIPTION OF THE DRAWINGS

The accompanying photographic drawings illustrate the new variety at close to one year of age, with the color being as nearly true as is possible with color illustrations of this type.

DESCRIPTION OF THE PLANT

Figure 1:
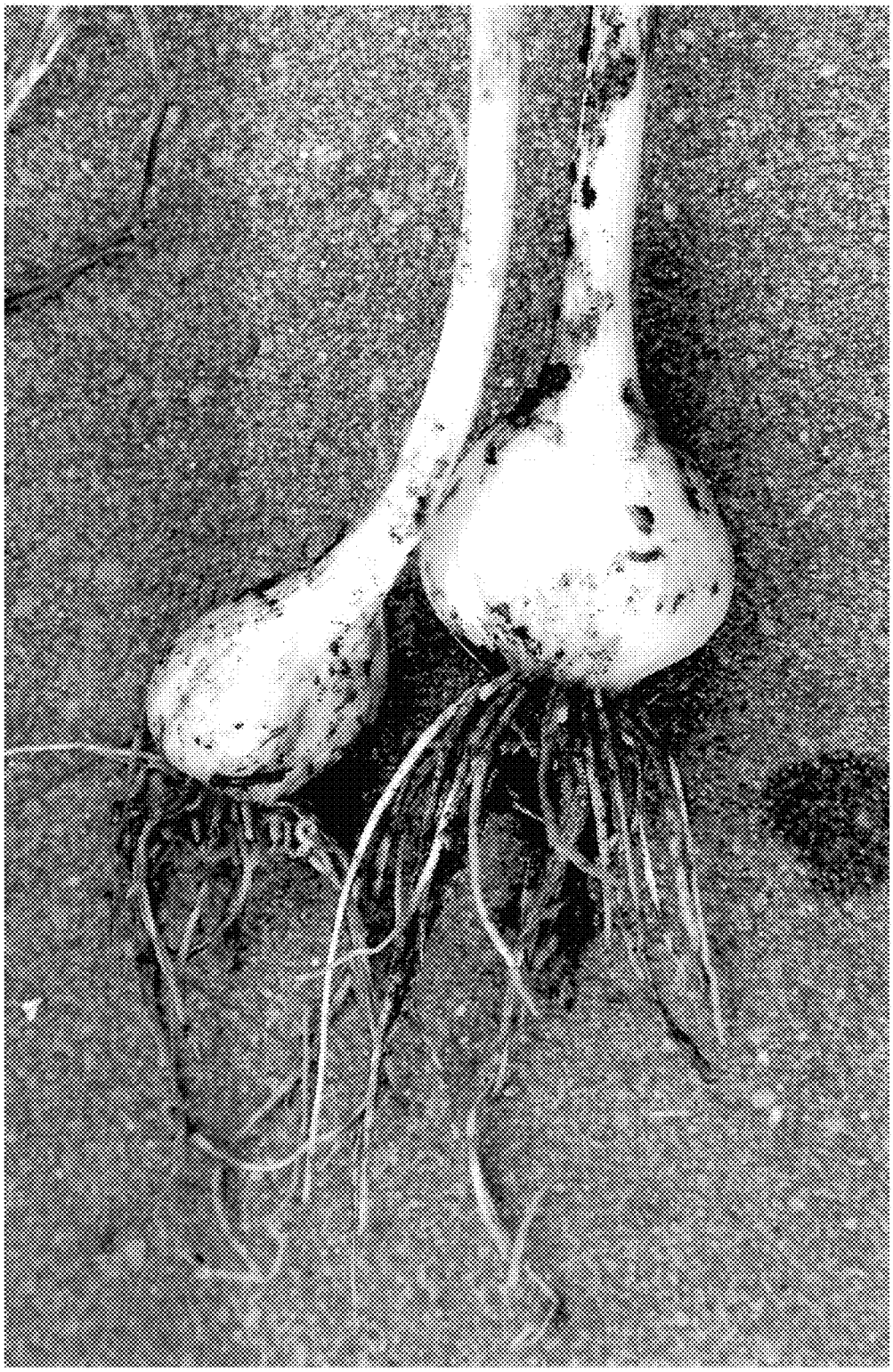
FIG. 1 shows a close-up view of bulbs of the new variety.
Figure 2:
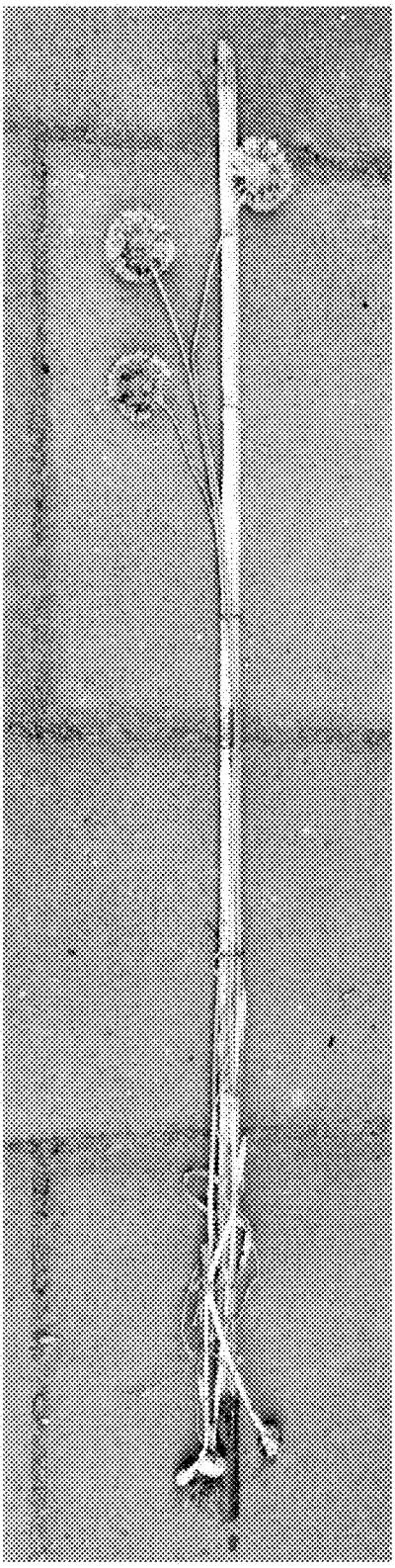
FIG. 2 shows freshly picked spears of the new variety.
Figure 3:
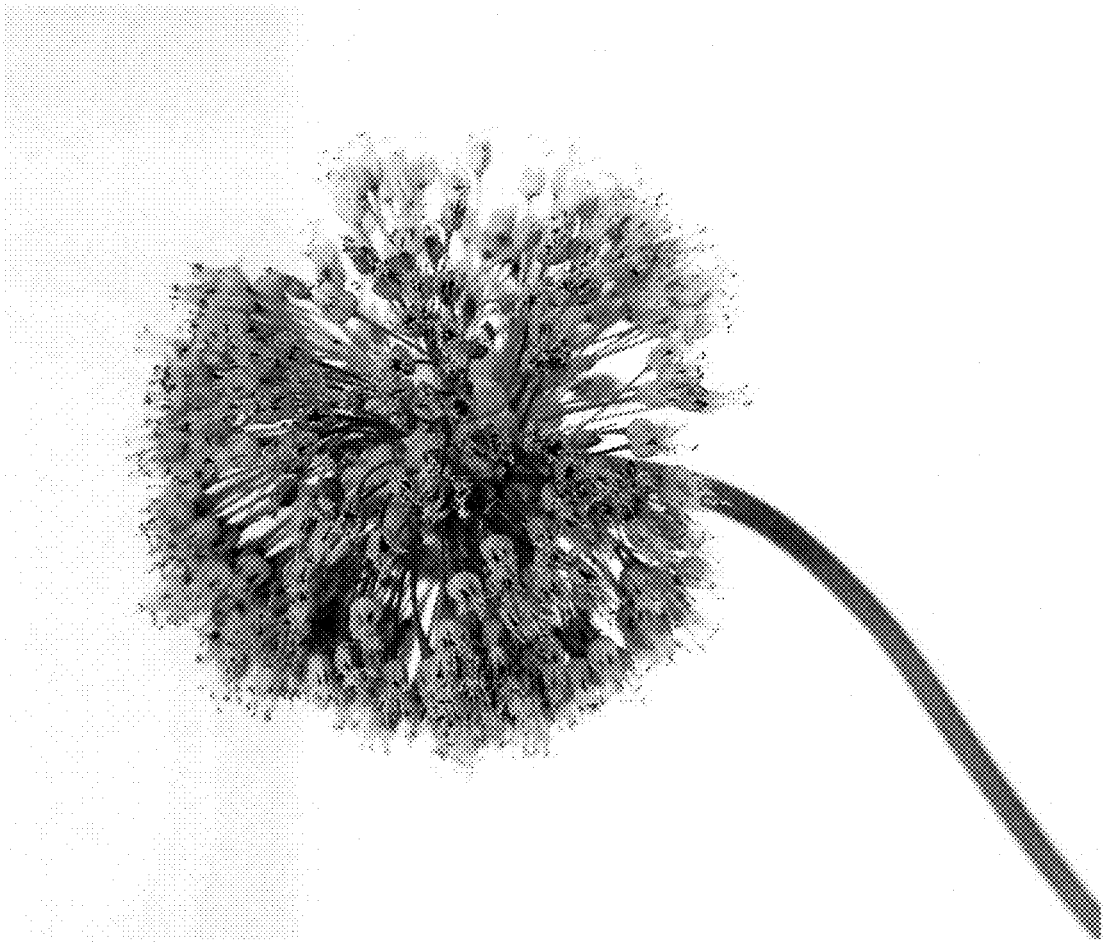
FIG. 3 shows a close-up view of an inflorescence of the new variety.

The following detailed description sets forth the characteristics of the new variety. Plants of the new variety were grown in well-drained, loamy, clay soil in the Netherlands under open field conditions under natural light. Growth conditions for 'BGS 352' were maritime climatic conditions in a long-day region with the sun at a 44° N sun angle and temperatures ranging from approximately 5 to 25° C. Planting of bulbs can occur as early as the middle of October, with the harvest of bulbs around the middle of June under Northern European conditions. Blooming following planting occurs around weeks 29/30. The color readings and measurements were taken in the Netherlands under natural light on close to one year old plants. Color references are primarily to The 2019 R.H.S. Colour Chart of The Royal Horticultural Society of London, Sixth Edition.

PLANT

Growth habit: Narrow and upright.

*Arrangement.*—An inflorescence is located at the top of a single stem growing from the base where the bulbs and roots are present.

*Height.*—Soil level to top of foliar plane: Average of 67.0 cm. Soil level to top of floral plane: Average of 127.0 cm.

*Spread.*—Average of 16.5 cm.

*Rooting.*—Fibrous.

*Productivity of plant (average weight per acre).*—Approximately 4,900 kg/acre.

*End of dormancy of cloves in bulb.*—Around the end of December, depending on storage conditions.

*Emergence speed after planting*.—Slow development after transplanting, depending on weather conditions.

*Disease/pest resistance/susceptibility*.—Nothing unusual observed to date.

Leaves:

*Number*.—Varies between 4 to 6.

*Length*.—Average of 22.8 cm (excluding the sheath).

*Width*.—Average of 0.8 cm.

*Aspect*.—Slight to moderately arching.

*Shape*.—Ligulate.

*Base*.—Sheathing present.

*Apex*.—Narrowly acuminate.

*Venation*.—Parallel.

*Margin*.—Minutely dentate, with teeth smaller than 0.1 mm.

*Fragrance*.—Very faint, somewhat garlic-like, and sweet.

*Attachment and arrangement*.—Along the flowering stem and alternate.

*Texture*.—Upper surface: Smooth, glabrous, and with no pubescence present. A very thin waxy layer of RHS 191B covers the surface. Lower surface: Smooth, glabrous.

*Color*.—Upper surface: RHS 144A. Lower surface: RHS 137B to 137C.

Bulbs:

*Transverse section shape*.—Broadly elliptic.

*Shape of apex*.—Narrowing.

*Shape of base*.—Rounded.

*Length*.—Average of 3.5 cm.

*Diameter*.—Average of 2.1 cm.

*Color of dry external scales*.—A blend of 155A and 158D.

*Dry external scale texture*.—Smooth, glabrous.

Cloves:

*Shape*.—Flattened on one side and rounded on the other.

*Length*.—Average of 3.1 cm.

*Diameter*.—Average of 1.8 cm at widest point; Average of 1.2 cm at narrowest point.

*Color of scale*.—RHS 160D, with the flattened side fading to RHS 186A and RHS 187C and 187D at the base.

*Taste*.—Typical garlic.

*Smell*.—Typical garlic.

*Eating quality*.—Good.

*Keeping quality*.—Good.

Inflorescence/flowers:

*Inflorescence type*.—Umbel.

*Flowering time*.—July/August in the Netherlands.

*Inflorescence number per stem*.—1.

*Inflorescence*.—Shape: Flattened globular. Number of flowers: Average of 400. Height: Average of 6.2 cm (excluding the peduncle). Diameter: Average of 7.0 cm. Fragrance: Very faint, somewhat garlic-like, and sweet.

*Flower bud*.—Length: Average of 3.25 mm. Width: Average of 1.5 mm. Shape: Obovate; triangular in cross-section. Color: RHS 70C.

*Flower*.—Form: Single. Length: Average of 0.6 cm. Width: Average of 0.4 cm.

*Petals*.—Not present. The perianth consists of only single whorls of tepals. There are no separate petals and sepals.

*Tepals*.—Number: Average of 6 per flower. Shape: Ovate and slightly concave. Length: Average of 3.5 mm. Average of 1.25 mm. Apex: Acute. Base: Broadly cuneate. Margin: Entire. Color: Upper surface: RHS 77D, fading lighter at the base. Lower surface: RHS 77C, fading to 77D at the base. Texture (both surfaces): Smooth, glabrous.

*Flower stem*.—Length: Average of 118.0 cm. Diameter: Average of 0.5 cm. Surface: Smooth, glabrous texture covered with a very thin waxy layer of RHS 191C. Slight gloss is present, but not visible due to the waxy layer. Color: RHS 145A.

*Pedicels*.—Length: Average of 2.5 cm. Width: Average: 0.75 mm. Surface: Smooth, glabrous, and moderately glossy. Strength: High. Color: Slightly lighter than RHS 186D, fading to RSH 143A and 143B at the proximal and distal end.

*Gynoecium*.—Pistils: Number: Average of 1. Length: Average of 4.0 mm. Stigma: Width: Average of 0.2 mm. Color: RHS NN155D. Styles: Length: Average of 3.5 mm. Color: RHS NN155D. Ovary: Diameter: Average of 0.35 cm. Color: RHS 146B with RHS 145C veins.

*Androecium*.—Stamens: Number: Average of 6 with the filament epipetalous. Shape: Laciniate. Anthers: Length: Average of 0.5 mm. Color: RHS 161B. Pollen: Low amount present. Filaments: Length: Average of 3.0 mm. Color: RHS NN155D.

*Seeds*.—Not present.

We claim:

1. A new and distinct variety of *Allium sativum* garlic plant named 'BGS 352', as is herein illustrated and described.

* * * * *